United States Patent
Suga et al.

(10) Patent No.: US 7,419,810 B2
(45) Date of Patent: Sep. 2, 2008

(54) ARGININE REPRESSOR DEFICIENT STRAIN OF CORYNEFORM BACTERIUM AND METHOD FOR PRODUCING L-ARGININE

(75) Inventors: Mikiko Suga, Kawasaki (JP); Yoko Asakura, Kawasaki (JP); Yukiko Mori, Kawasaki (JP); Hisao Ito, Kawasaki (JP); Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 17 days.

(21) Appl. No.: 11/451,347

(22) Filed: Jun. 13, 2006

(65) Prior Publication Data
US 2007/0031946 A1 Feb. 8, 2007

Related U.S. Application Data

(62) Division of application No. 09/835,381, filed on Apr. 17, 2001, now Pat. No. 7,160,705.

(30) Foreign Application Priority Data
Apr. 28, 2000 (JP) .............................. 2000-129167

(51) Int. Cl.
- *C12P 13/10* (2006.01)
- *C12N 1/00* (2006.01)
- *C12N 1/20* (2006.01)
- *C07K 1/00* (2006.01)
- *C07H 21/04* (2006.01)

(52) U.S. Cl. .................... 435/114; 435/243; 435/252.1; 435/252.3; 435/252.32; 435/320.1; 435/440; 435/455; 530/350; 536/23.7

(58) Field of Classification Search ................. 435/114, 435/243, 252.1, 252.3, 252.32, 320.1, 440, 435/455; 530/350; 536/23.7
See application file for complete search history.

(56) References Cited

U.S. PATENT DOCUMENTS

| 3,878,044 | A | 4/1975 | Kubola et al. |
| 4,775,623 | A | 10/1988 | Katsumata et al. |
| 2003/0124686 | A1 | 7/2003 | Suga et al. |

FOREIGN PATENT DOCUMENTS

| EP | 0 259 858 | 3/1988 |
| EP | 0 261 627 | 3/1988 |
| EP | 0 443 031 | 8/1991 |
| JP | 5-23750 | 2/1993 |

OTHER PUBLICATIONS

Lim et al. Proc Natl Acad Sci U S A. Oct. 1987;84(19):6697-701.*
H. Yoshida, et al., Agric. Biol. Chem., vol. 43, No. 1, pp. 105-111, "Mechanism of L-Arginine Production by L-Arginine-Producing Mutants of *Corynebacterium glutamicum*", 1979.
D. Lim, et al., Proc. Natl. Acad. Sci. USA, vol. 84, pp. 6697-6701, "Nucleotide Sequence of the ARGR Gene of *Escherichia coli* K-12 and Isolation of its Product, the Arginine Repressor", Oct. 1987.
D. Charlier, et al., J. Mol. Biol., vol. 226, pp. 367-386, "Arginine Regulon of *Escherichia coli* K-12, A Study of Repressor-Operator Interactions and of In Vitro Binding Affinities Versus In Vivo Repression", 1992.
Makarova et al., "Conservation of the Binding Site for the Arginine Repressor in all Bacteriallineages", Genome Biol 2001; 2(4): Research0013.
Database EMBL Online! Jan. 6, 1999, Ko, S.Y., et al., "*Corynebacterium glutamicum* Arginine repressor (ARGR) Gene, Complete CDS." retrieved from EBI Database accession No. AF041436 XP002221143.
G. Tian, et al., "Mutational Analysis of the Arginine Repressor of *Escherichia coli*", Molecular Microbiology, England, Aug. 1994, vol. 13, No. 4, pp. 599-608.
F. Messenguy, et al., "Determination of the DNA-Binding Sequences of ARGR Proteins to Arginine Anabolic and Catabolic Promoters", Molecular and Cellular Biology, USA, May 1991, vol. 11, No. 5, pp. 2852-2863.
A. Maghnouj, et al., Journal of Bacteriology, vol. 180, No. 24, pp. 6468-6475, "The Arcabdc Gene Cluster, Encoding the Arginine Deiminase Pathway of *Bacillus licheniforms*, and its Activation by the Arginine Repressor ARGR", Dec. 1998.
U.S. Appl. No. 11/451,347, filed Jun. 13, 2006, Suga et al.
U.S. Appl. No. 09/432,126, filed Nov. 2, 1999, Suga et al.

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

L-Arginine is produced by culturing a coryneform bacterium in which an arginine repressor involved in L-arginine biosynthesis is deleted by disrupting a gene coding for the repressor, and which has L-arginine producing ability in a medium to produce and accumulate L-arginine in the medium, and collecting the L-arginine from the medium.

8 Claims, 2 Drawing Sheets

ARGININE REPRESSOR DEFICIENT STRAIN OF CORYNEFORM BACTERIUM AND METHOD FOR PRODUCING L-ARGININE

This application is divisional application of U.S. application Ser. No. 09/835,381, now U.S. Pat. No. 7,160,705, filed on Apr. 17, 2001, which claims priority to JP 2000-129167, filed on Apr. 28, 2000.

FIELD OF THE INVENTION

The present invention relates to a coryneform bacterium having an ability to produce L-arginine and a method for producing L-arginine using the bacterium. L-arginine is an industrially useful amino acid as an ingredient of liver function promoting agents, amino acid infusions, comprehensive amino acid pharmaceuticals and so forth.

DESCRIPTION OF THE RELATED ART

Conventional L-arginine production by fermentation has been performed by utilizing wild-type strains of coryneform bacteria; coryneform bacteria resistant to certain agents including sulfa drugs, 2-thiazolealanine, á-amino-á-hydroxyvaleric acid and the like; coryneform bacteria exhibiting auxotrophy for L-histidine, L-proline, L-threonine, L-isoleucine, L-methionine, or L-tryptophan in addition to the resistance to 2-thiazolealanine (Japanese Patent Laid-open No. 54-44096); coryneform bacteria resistant to ketomalonic acid, fluoromalonic acid, or monofluoroacetic acid (Japanese Patent Laid-open No. 57-18989); coryneform bacteria resistant to argininol (Japanese Patent Laid-open No. 62-24075); coryneform bacteria resistant to X-guanidine (X represents a derivative of fatty acid or aliphatic chain, Japanese Patent Laid-open No. 2-186995) or the like.

On the other hand, there have also been disclosed methods for producin g L-arginine utilizing recombinant DNA techniques. That is, there has been disclosed a method for producing L-arginine by utilizing a microorganism belonging to the genus *Corynebacterium* or *Brevibacterium* which is made to harbor a recombinant DNA comprising a vector DNA and a DNA fragment containing genes for acetylornithine deacetylase, N-acetylglutamic acid-â-semialdehyde dehydrogenase, N-acetyl glutamokinase, and argininosuccinase derived from a microorganism belonging to the genus *Escherichia* (Japanese Patent Publication No. 5-23750).

Further, as for coryneform bacteria, it has been elucidated that synthesis of some enzymes of the L-arginine biosynthetic system is repressed by L-arginine. Furthermore, it was reported that, while some of enzymes of L-arginine biosynthetic system were repressed by L-arginine, the repression of these enzymes by L-arginine was canceled in mutant strains of coryneform bacteria showing improved L-arginine accumulation amounts (*Agric. Biol. Chem.*, 43(1), 105, 1979).

Meanwhile, as for *Escherichia coli*, a repressor of L-arginine biosynthetic system and a gene coding for the repressor were identified (*Proc. Natl. Acad. Sci. U.S.A.* (1987), 84(19), 6697-701), and binding interactions of the repressor protein and various genes of L-arginine biosynthetic system were also investigated (*Proc. Natl. Acad. Sci. U.S.A.* (1987), 84(19), 6697-701, *J. Mol. Biol.* (1992), 226, 367-386).

However, any repressor proteins of the L-arginine biosynthetic system have not been identified in coryneform bacteria. While a nucleotide sequence of the repressor protein gene (argR) and an amino acid sequence assumed to be encoded thereby are registered in a gene database, GenBank (AF049897), the gene is considered to be designated argR because of the homology between the aforementioned amino acid sequence and known arginine repressors.

SUMMARY OF THE INVENTION

As described above, although a repressor protein of the L-arginine biosynthetic system of coryneform bacteria and a gene thereof are expected, the repressor protein itself has not been identified and its functions and so forth are not elucidated at all. Therefore, an object of the present invention is to identify the repressor of the L-arginine biosynthesis in coryneform bacteria, and improve L-arginine productivity of coryneform bacteria.

The inventors of the present invention isolated a homologue of the gene registered as argR in the gene database (GenBank accession AF049897) from a coryneform bacterium, and found that, if this gene was amplified in coryneform bacteria, L-arginine producing ability was decreased, and on the other hand, if the gene was disrupted, the L-arginine producing ability was improved, to confirm that the L-arginine biosynthesis is repressed by a repressor in coryneform bacteria like *Escherichia coli* and the aforementioned gene registered as argR codes for the repressor. Thus, the present invention was accomplished.

That is, the present invention provides the followings.

(1) A coryneform bacterium in which an arginine repressor does not function in a normal manner, and which has L-arginine producing ability.

(2) The coryneform bacterium according to (1), wherein the arginine repressor does not function in a normal manner due to disruption of a gene coding for the arginine repressor on a chromosome of the bacterium.

(3) The coryneform bacterium according to (2), wherein the arginine repressor has the amino acid sequence shown in SEQ ID NO: 18 or an amino acid sequence showing homology to the amino acid sequence.

(4) A method for producing L-arginine, which comprises culturing a coryneform bacterium according to any one of (1) to (3) in a medium to produce and accumulate L-arginine in the medium, and collecting the L-arginine from the medium.

In the present invention, the "arginine repressor" refers to a protein that has an effect of repressing the L-arginine biosynthesis, and if expression amount of the gene that codes for the protein increases in coryneform bacteria, L-arginine producing ability will be reduced, and if the expression amount decreases or the protein disappears, the L-arginine producing ability will be improved. Hereafter, the gene coding for the arginine repressor is also called argR gene. Further, the "L-arginine producing ability" used in the present invention refers to an ability of the microorganism of the present invention to accumulate L-arginine in a medium, when it is cultured in the medium.

According to the present invention, L-arginine producing ability of coryneform bacteria having the L-arginine producing ability can be improved.

Figure 1:
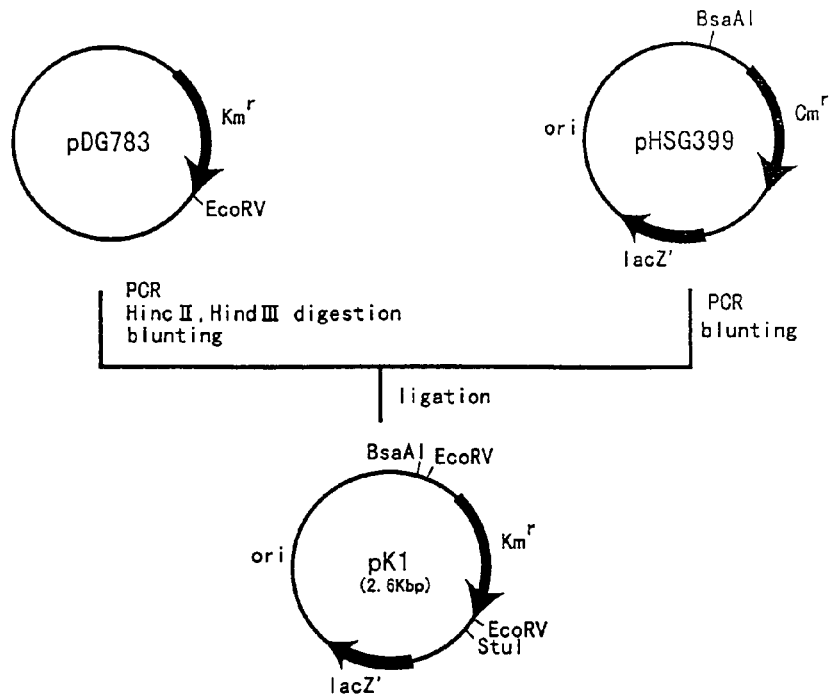
FIG. 1 shows the construction process of plasmid pK1.

The coryneform bacteria include bacteria having been hitherto classified into the genus *Brevibacterium* but united into the genus *Corynebacterium* at present (*Int. J. Syst. Bacteriol.*, 41, 255 (1981)), and include bacteria belonging to the genus *Brevibacterium* closely relative to the genus *Corynebacterium*. Examples of such coryneform bacteria include the followings.

Corynebacterium acetoacidophilum
Corynebacterium acetoglutamicum
Corynebacterium alkanolyticum
Corynebacterium callunae
Corynebacterium glutamicum
Corynebacterium lilium (Corynebacterium glutamicum)
Corynebacterium melassecola
Corynebacterium thermoaminogenes
Corynebacterium herculis
Brevibacterium divaricatum
(Corynebacterium glutamicum)
Brevibacterium flavum (Corynebacterium glutamicum)
Brevibacterium immariophilum
Brevibacterium lactofermentum
(Corynebacterium glutamicum)
Brevibacterium roseum
Brevibacterium saccharolyticum
Brevibacterium thiogenitalis
Brevibacterium album
Brevibacterium cerinum
Microbacterium ammoniaphilum While the coryneform bacteria that have the L-arginine-producing ability are not particularly limited so long as they have the L-arginine-producing ability, they include, for example, wild-type strains of coryneform bacteria; coryneform bacteria resistant to certain agents including sulfa drugs, 2-thiazolealanine, α-amino-β-hydroxyvaleric acid and the like; coryneform bacteria exhibiting auxotrophy for L-histidine, L-proline, L-threonine, L-isoleucine, L-methionine, or L-tryptophan in addition to the resistance to 2-thiazolealanine (Japanese Patent Laid-open No. 54-44096); coryneform bacteria resistant to ketomalonic acid, fluoromalonic acid, or monofluoroacetic acid (Japanese Patent Laid-open No. 57-18989); coryneform bacteria resistant to argininol (Japanese Patent Laid-open No. 62-24075); coryneform bacteria resistant to X-guanidine (X represents a derivative of fatty acid or aliphatic chain, Japanese Patent Laid-open No. 2-186995) and the like.

Specifically, the following strains can be exemplified.
Brevibacterium flavum AJ11169 (BP-6892)
Corynebacterium glutamicum AJ12092 (FERM BP-6906)
Brevibacterium flavum AJ11336 (FERM BP-6893)
Brevibacterium flavum AJ11345 (FERM BP-6894)
Corynebacterium glutamicum AJ12430 (FERM BP-2228)

The AJ11169 strain and the AJ12092 strain are the 2-thiazolealanine resistant strains mentioned in Japanese Patent Laid-open No. 54-44096, the AJ11336 strain is the strain having argininol resistance and sulfadiazine resistance mentioned in Japanese Patent Publication No. 62-24075, the AJ11345 strain is the strain having argininol resistance, 2-thiazolealanine resistance, sulfaguanidine resistance, and exhibiting histidine auxotrophy mentioned in Japanese Patent Publication No. 62-24075, and the AJ12430 strain is the strain having octylguanidine resistance and 2-thiazolealanine resistance mentioned in Japanese Patent Laid-open No. 2-186995.

AJ11169 was deposited on Aug. 3, 1977 in National Institute of Bioscience and Human Technology, Agency of Industrial Science and Technology, Ministry of International Trade and Industry (currently National Institute of Bioscience and Human Technology, National Institute of Advanced Industrial Science and Technology, Ministry of Economy, Trade and Industry)(zip code: 305-8566, 1-3 Higashi 1-Chome, Tsukuba-shi, Ibaraki-ken, Japan), as deposition number of FERM P-4161, and transferred from the original deposit to international deposit based on Budapest Treaty on Sep. 27, 1999, and has been deposited as deposition number of FERM BP-6892.

AJ12092 was deposited on Sept. 29, 1983 in National Institute of Bioscience and Human Technology, Agency of Industrial Science and Technology, Ministry of International Trade and Industry, as deposition number of FERM P-7273, and transferred from the original deposit to international deposit based on Budapest Treaty on Oct. 1, 1999, and has been deposited as deposition number of FERM BP-6906.

AJ11336 was deposited on Apr. 25, 1979 in National Institute of Bioscience and Human Technology, Agency of Industrial Science and Technology, Ministry of International Trade and Industry, as deposition number of FERM P-4939, and transferred from the original deposit to international deposit based on Budapest Treaty on Sep. 27, 1999, and has been deposited as deposition number of FERM BP-6893.

AJ11345 was deposited on Apr. 25, 1979 in National Institute of Bioscience and Human Technology, Agency of Industrial Science and Technology, Ministry of International Trade and Industry, as deposition number of FERM P-4948, and transferred from the original deposit to international deposit based on Budapest Treaty on Sep. 27, 1999, and has been deposited as deposition number of FERM BP-6894.

AJ12430 was deposited on Dec. 26, 1988 in National Institute of Bioscience and Human Technology, Agency of Industrial Science and Technology of Ministry, International Trade and Industry based on Budapest Treaty, as deposition number of FERM BP-2228.

The coryneform bacterium whose arginine repressor does not function in a normal manner can be obtained by modifying its argR gene so that the activity of the arginine repressor should be reduced or eliminated, or the transcription of the argR gene should be reduced or eliminated. Such a coryneform bacterium can be obtained by, for example, replacing the chromosomal argR gene with an argR gene that does not function in a normal manner (occasionally referred to as "disrupted argR gene" hereinafter) through, for example, homologous recombination based on genetic recombination techniques (Experiments in Molecular Genetics, Cold Spring Harbor Laboratory Press (1972); Matsuyama, S. and Mizushima, S., *J. Bacteriol.*, 162, 1196 (1985)).

In the homologous recombination, when a plasmid carrying a sequence exhibiting homology with a chromosomal sequence or the like is introduced into a corresponding bacterial cell, recombination occurs at a site of the homologous sequence at a certain frequency, and thus the introduced plasmid as a whole is integrated into the chromosome. Then, by causing recombination again at the site of the homologous sequence in the chromosome, the plasmid may be removed from the chromosome. However, depending on the position at which the recombination is caused, the disrupted gene may remain on the chromosome, while the original normal gene may be removed from the chromosome together with the plasmid. By selecting such a bacterial strain, a bacterial strain in which the normal argR gene is replaced with a disrupted argR gene can be obtained.

Such a gene disruption technique based on the homologous recombination has already been established, and a method utilizing a linear DNA, method utilizing temperature sensitive plasmid or the like can be used therefor. The argR gene can also be disrupted by using a plasmid that contains the argR gene inserted with a marker gene such as drug resistance gene, and cannot replicate in a target cell of the coryneform bacterium. That is, in a transformant that has been transformed with such a plasmid and hence acquired drug resistance, the marker gene is integrated in a chromosome DNA. It is likely that this marker gene has been integrated by homologous recombination of the argR gene present at the both sides of the marker with the argR on the chromosome, and therefore a gene-disrupted strain can efficiently be selected.

Specifically, a disrupted argR gene used for the gene disruption can be obtained by deletion of a certain region of argR gene by means of digestion with restriction exzyme(s) and religation; by insertion of another DNA fragment (marker gene etc.) into the argR gene, by introducing substitution, deletion, insertion, addition or inversion of one or more nucleotides in a nucleotide sequence of coding region of argR gene, its promoter region or the like by means of site-specific mutagenesis (Kramer, W. and Frits, H. J., *Methods in Enzymology*, 154, 350 (1987)) or treatment with a chemical reagent such as sodium hyposulfite and hydroxylamine (Shortle, D. and Nathans, D., *Proc. Natl. Acad. Sci. U.S.A.*, 75, 270(1978)) or the like, so that the activity of the encoded repressor should be reduced or eliminated, or transcription of the argR gene should be reduced or eliminated. Among these embodiments, a method utilizing deletion of a certain region of the argR gene by digestion with a restriction enzyme and religation, or insertion of another DNA fragment into the argR gene is preferred in view of reliability and stability.

A plasmid for the argR gene disruption can be produced by performing PCR (polymerase chain reaction) using a plasmid containing the argR gene and its flanking regions as a template and primers corresponding the terminal portions or franking regions of the argR gene to amplify a portion except for an internal portion or the whole portion of the argR gene, and cyclizing the obtained amplified product. In the examples mentioned hereinafter, the argR gene was disrupted by this method.

The argR gene can be obtained from a chromosomal DNA of a coryneform bacterium by PCR using oligonucleotides prepared based on known nucleotide sequences of the argR gene as primers. The argR gene can also be obtained from a chromosome DNA library of a microorganism which has a purine operon by a hybridization technique using an oligonucleotide prepared based on a known nucleotide sequence of the argR gene as a probe. For the purpose of the present invention, because the argR gene is used for preparing a disrupted argR gene, it is not necessarily required to contain the full length, and it may contain a length required to cause gene disruption.

The origin of the argR gene is not particularly limited, so long as it has such a degree of homology that it should cause homologous recombination with the argR gene of coryneform bacteria. Specifically, the argR gene of the Brevibacterium flavum, which has the nucleotide sequence shown in SEQ ID NO: 17, and the argR gene of Corynebacterium glutamicum (GenBank accession AF049897) can be mentioned as the argR genes of coryneform bacteria. These argR genes are highly homologous, and it is considered that even an argR gene of coryneform bacterium of a genus or species different from that of a coryneform bacterium of which argR gene is to be disrupted may also be used for the gene disruption.

In the present invention, the amino acid sequence shown in SEQ ID NO: 18 or an amino acid sequence exhibiting homology to the amino acid sequence means an amino acid sequence that is encoded by an argR gene having such a degree of homology that it should cause homologous recombination with the argR gene coding to the amino acid sequence shown in SEQ ID NO: 18 (for example, an argR gene having the nucleotide sequence shown in SEQ ID NO: 17).

As the primers used for PCR, any primers that allow amplification of the argR gene can be used. Specific examples thereof include the oligonucleotides having the nucleotide sequences shown in SEQ ID NOS: 19 and 20.

Further, examples of marker gene include drug resistance genes such as a kanamycin resistance gene. A kanamycin resistance gene can be obtained by PCR amplification from a known plasmid containing a kanamycin resistance gene of *Streptococcus faecalis*, for example, pDG783 (Anne-Marie Guerout-Fleury et al., *Gene*, 167, 335-337 (1995)).

When a drug resistance gene is used as the marker gene, an argR gene-disrupted strain can be obtained by inserting the drug resistance gene into a suitable site of the argR gene carried by a plasmid, transforming a microorganism with the plasmid, and selecting a drug resistant transformant. Disruption of argR gene on a chromosome can be confirmed by analyzing the argR gene or the marker gene on the chromosome by Southern blotting, PCR, or the like. Integration of the kanamycin resistance gene into a chromosomal DNA can be confirmed by PCR using primers that allow amplification of the kanamycin resistance gene (e.g., oligonucleotides having nucleotide sequences shown in SEQ ID NOS: 1 and 2).

L-arginine can be efficiently produced by culturing a coryneform bacterium having L-arginine producing ability obtained as described above, in which an arginine repressor does not function in a normal manner, in a medium to produce and accumulate L-arginine in the medium, and collecting the L-arginine from the medium.

The medium to be used may be selected from well-known media conventionally used for fermentative production of amino acids utilizing microorganisms. That is, it may be a usual medium that contains a carbon source, nitrogen source, inorganic ions, and other organic ingredients as required.

As the carbon source, there can be used saccharides such as glucose, sucrose, lactose, galactose, fructose or starch hydrolysate, alcohols such as glycerol or sorbitol, or organic acids such as fumaric acid, citric acid or succinic acid.

As the nitrogen source, there can be used inorganic ammonium salts such as ammonium sulfate, ammonium chloride or ammonium phosphate, organic nitrogen such as soybean protein hydrolysate, ammonia gas, aqueous ammonia and so forth.

It is desirable to add required substances such as vitamin $B_1$ and L-homoserine, yeast extract and so forth to the medium in appropriate amounts as organic trace nutrients. Other than the above, potassium phosphate, magnesium sulfate, iron ion, manganese ion and so forth are added in small amounts as required.

The culture is preferably carried out under an aerobic condition for 1-7 days. The culture temperature is preferably controlled to be 24° C. to 37° C., and pH is preferably controlled to be 5-9 during the culture. Inorganic or organic, acidic, alkaline substances, or ammonia gas and so forth can be used for pH adjustment. L-arginine can be collected from the fermentation broth usually by a combination of well-known techniques such as ion exchange resin techniques and other techniques.

BEST MODE FOR CARRYING OUT THE INVENTION

Hereafter, the present invention will be explained more specifically with reference to the following examples.

EXAMPLE 1

Constructions of Shuttle Vector for *Escherichia coli* and coryneform Bacteria and Temperature Sensitive Vector First, a vector for introducing an argR gene into coryneform bacteria and a temperature sensitive vector for producing an argR deficient strain of coryneform bacterium were constructed.

<1> Construction of Vector Having Drug Resistance Gene of *Streptococcus faecalis*

The kanamycin resistance gene of *Streptococcus faecalis* was amplified by PCR from a known plasmid containing the gene. The nucleotide sequence of the kanamycin resistance gene of *Streptococcus faecalis* has already been elucidated (Trieu-Cuot, P. and Courvalin, P.: *Gene*, 23 (3), 331-341 (1983)). Based on this sequence, the primers shown in SEQ ID NOS: 1 and 2 were synthesized, and PCR was performed by using pDG783 (Anne-Marie Guerout-Fleury, et al., *Gene*, 167, 335-337 (1995)) as a template to amplify a DNA fragment containing the kanamycin resistance gene and its promoter.

The aforementioned DNA fragment was purified by using SUPREC02 produced by Takara Shuzo Co., Ltd., and then completely digested with restriction enzymes HindIII and HincII to be blunt-ended. The blunt-ending was performed by using Blunting Kit produced by Takara Shuzo Co., Ltd. This DNA fragment was mixed with a DNA fragment obtained by purification and blunt-ending of an amplification product of PCR performed by using the primers shown in SEQ ID NOS: 3 and 4 and pHSG399 (see S. Takeshita, et al.: *Gene*, 61, 63-74 (1987)) as a template, and ligated both fragments. The ligation was performed by using DNA Ligation Kit Ver. 2 produced by Takara Shuzo Co., Ltd. Competent cells of *Escherichia coli* JM109 (produced by Takara Shuzo Co., Ltd.) were transformed with the ligated DNA, plated on L medium (10 g/L of Bacto trypton, 5 g/L of Bacto yeast extract, 5 g/L of NaCl, 15 g/L of agar, pH 7.2) containing 10 µg/ml of IPTG (isopropyl-â-D-thiogalactopyranoside), 40 µg/ml of X-Gal (5-bromo-4-chloro-3-indolyl-â-D-galactoside) and 25 µg/ml of kanamycin, and cultured overnight. The emerged blue colonies were picked up, and separated into single colonies to obtain transformant strains.

Plasmids were prepared from the transformant strains by the alkali method (Seibutsu Kogaku Jikkensyo (Text for Bioengineering Experiments), Edited by the Society for Bioscience and Bioengineering, Japan, p.105, Baifukan, 1992), and restriction maps were prepared. One having a restriction map equivalent to that of FIG. 1 was designated as pK1. This plasmid is stably harbored in *Escherichia coli*, and imparts kanamycin resistance to a host. Moreover, since it contains the lacZ' gene, it is suitably used as a cloning vector.

<2> Construction of Shuttle Vector pSFK6

Figure 2:
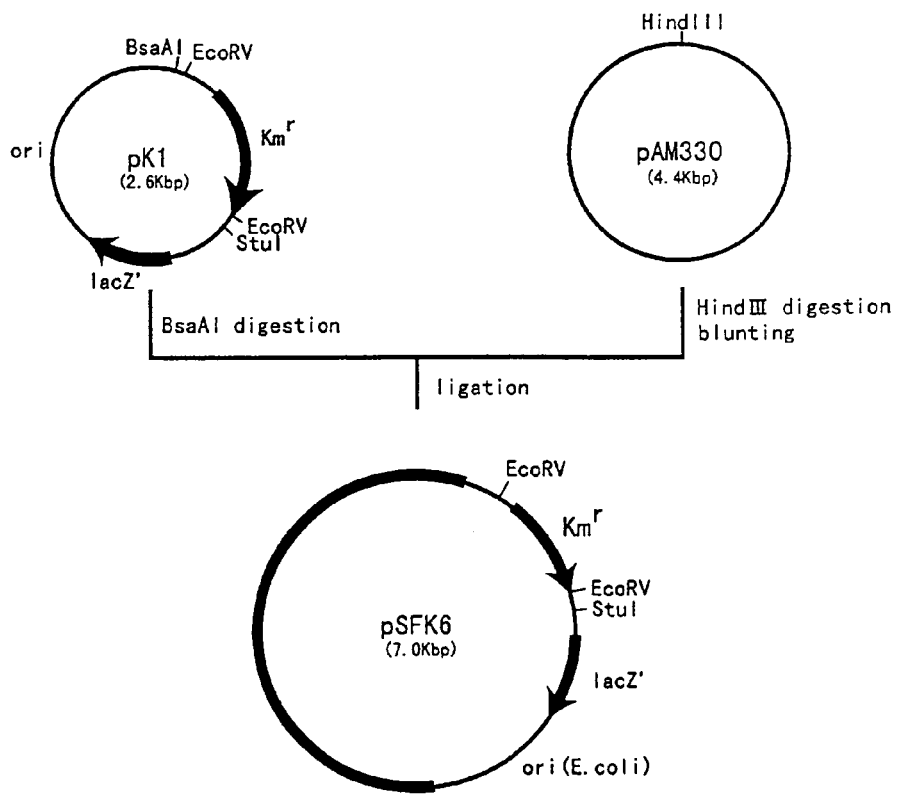
FIG. 2 shows the construction process of plasmid pSFK6.

As a material for obtaining a temperature sensitive replication control region, a plasmid vector autonomously replicable in both of *Escherichia coli* cells and coryneform bacteria cells was prepared. The plasmid pAM330 extracted from *Brevibacterium lactofermentum* ATCC13869 [see Japanese Patent Publication Laid-open (Kokai) No. 58-67699] was completely digested with a restriction enzyme HindIII, and blunt-ended. This fragment was ligated to a fragment obtained by completely digesting the aforementioned pK1 with a restriction enzyme BsaAI. *Brevibacterium lactofermentum* ATCC13869 was transformed with the ligated DNA. The transformation was performed by the electric pulse method [see Japanese Patent Publication Laid-open (Kokai) No. 2-207791]. Transformants were selected on an M-CM2B plate (10 g/L of polypeptone, 10 g/L of yeast extract, 5 g/L of NaCl, 10 µg/L of biotin, 15 g/L of agar, pH 7.2) containing 25 µg/ml of kanamycin. After cultivation for 2 days, colonies were picked up, and separated into single colonies to obtain the transformants. Plasmid DNAs were prepared from the transformants, and restriction maps were prepared. One having the same restriction map as that of FIG. 2 was designated as pSFK6. This plasmid is autonomously replicable in both of *Escherichia coli* and coryneform bacteria, and imparts kanamycin resistance to a host.

<3> Construction of a Plasmid Having Temperature Sensitive Replication Control Region pSFK6 was treated with hydroxylamine in vitro. The hydroxylamine treatment was performed according to a known method [see, for example, G. O. Humpherys, et al., Molec. Gen. Genet., 145, 101-108 (1976)]. DNA undergone the treatment was collected and used for transformation of *Brevibacterium lactofermentum* ATCC13869 strain. The transformants were selected at a low temperature (25° C.) on a CM2B plate containing 25 µg/ml of kanamycin. The appeared transformants were replicated to a similar selection plate, and cultured at an elevated temperature (34° C.). One strain that could not grow on the selection plate containing kanamycin at the elevated temperature was obtained. From this strain, a plasmid was recovered and designated as p48K.

<4> Determination of Nucleotide Sequence of Temperature Sensitive Replication Control Region Nucleotide sequences of replication control region segments in the plasmid pSFK6 having a wild-type replication control region and the plasmid p48K having a temperature sensitive replication control region were determined. The nucleotide sequences were determined on a fully automatic sequencer, ABI310 (ABI), by using DNA Sequencing Kit from ABI. As a result, it was found that there were 6 nucleotide substitutions between the wild-type replication control region and the temperature sensitive replication control region. The nucleotide sequence of the temperature sensitive replication control region segment contained in pSFK6 (derived from full sequence of pAM330), which functions in coryneform bacteria, is shown in SEQ ID NO: 5, and the nucleotide sequence of the temperature sensitive replication control region segment contained in p48K, which functions in coryneform bacteria, is shown in SEQ ID NO: 7. Further, the amino acid sequences encoded by ORFs contained in these nucleotide sequences are shown in SEQ ID NOS: 6 and 8. In the temperature sensitive replication control region, the 1255th C is mutated to T, the 1534th C to T, the 1866th G to A, the 2058th G to A, the 2187th C to T and 3193rd G to A. Among these, only the mutation at 1534th position is accompanied by an amino acid mutation, and causes substitution of serine for proline.

<5> Construction of Shuttle Vectors Having Temperature Sensitive Mutation

Figure 3:
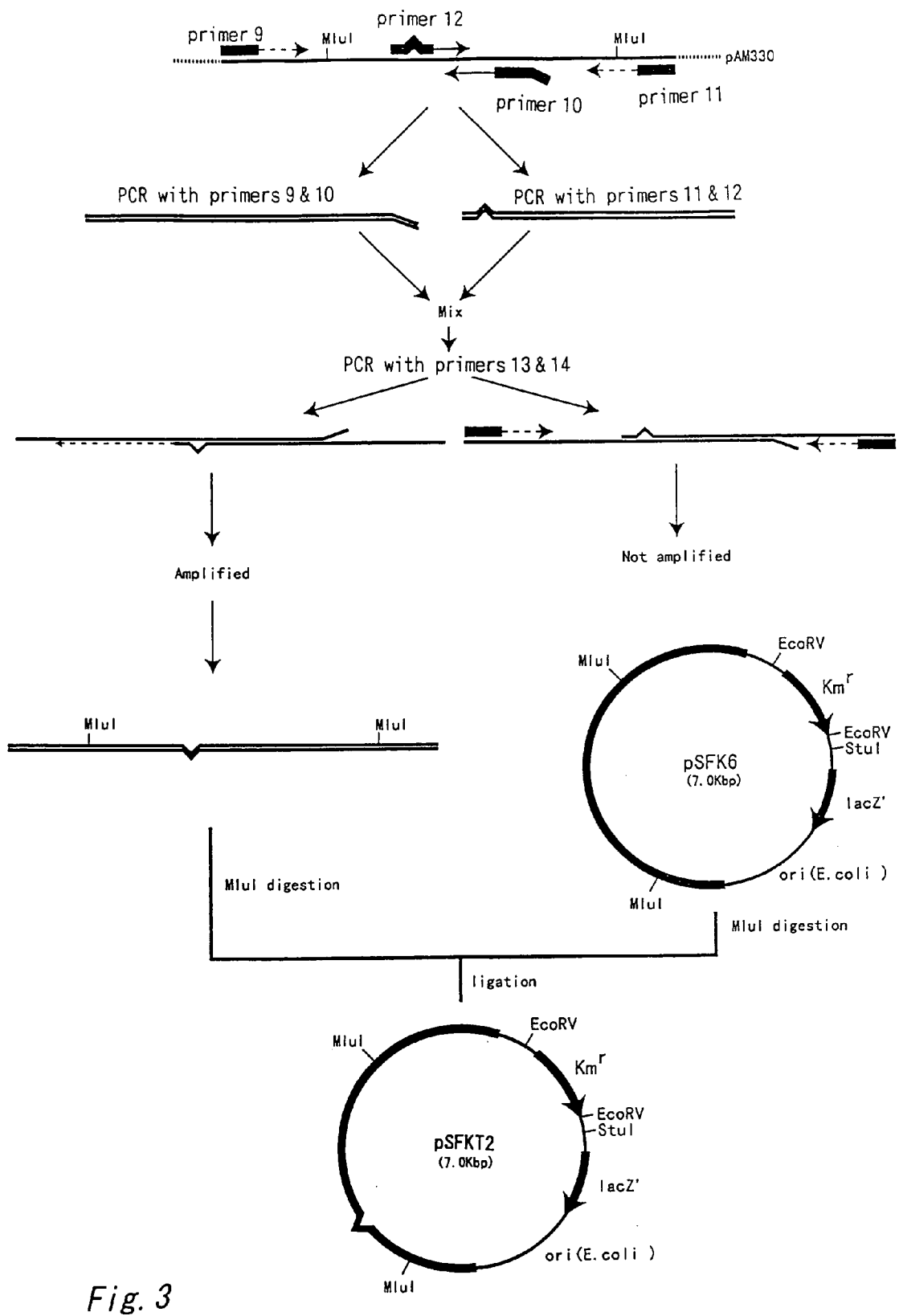
FIG. 3 shows the construction process of plasmid pSFKT2.
Hereafter, the present invention will be explained in detail.
The microorganism of the present invention is a coryneform bacterium having L-arginine producing ability, in which arginine repressor does not function in a normal manner. The coryneform bacterium of the present invention may be a microorganism having the L-arginine producing ability because an arginine repressor does not function in a normal manner in it, or a microorganism bred so that the arginine repressor should not function in a normal manner in it. Alternatively, it may be a microorganism that is bred so that the arginine repressor should not function in a normal manner in it and then imparted with the L-arginine producing ability.

Each one of the six mutations of p48K was introduced into a shuttle vector pSFK6 (see FIG. 3). The introduction of the mutations was performed by a known method [Mikaelian, I., Sergeant, A., *Nucleic Acids Res.*, 20, 376 (1992)]. Specific procedure will be mentioned below. In order to introduce the mutation of 1534th C to T, PCR was performed by using a combination of the primers shown in SEQ ID NOS: 9 and 10 (primers 9 and 10), and a combination of the primers shown in SEQ ID NOS: 11 and 12 (primers 11 and 12), and pAM330 as a template. Each of the obtained amplification products was purified by subjecting them to agarose gel electrophoresis, and collecting them from the gel. The collection of the DNA fragments from the gel was performed by using EASYTRAP Ver.2 (Takara Shuzo Co., Ltd.). The purified DNAs were mixed in a molar ratio of 1:1, and used as a template for PCR performed by using the primers shown SEQ ID NOS: 13 and 14 (primers 13 and 14). The amplification product was fully digested with a restriction enzyme MluI, and subjected to agarose gel electrophoresis to recover a DNA fragment of about 3.2 kb. Similarly, pSFK6 was also completely digested with a restriction enzyme MluI, and subjected to agarose gel electrophoresis to recover a DNA fragment of about 3.8 kb. The obtained DNA fragments were mixed and ligated, and used to transform competent cells of *Escherichia coli* JM109 (Takara Shuzo Co., Ltd.). The cells were applied on L medium containing 25 µg/ml of kanamycin, and cultured overnight. The appeared colonies were picked up, and isolated single colonies to obtain transformant strains. A plasmid was prepared from the transformant strains by the alkaline method, and the nucleotide sequence of the plasmid was determined to confirm that 1534th C in the sequence shown in SEQ ID NO: 5 was mutated to T. This plasmid was designated as pSFKT2 (FIG. 3).

EXAMPLE 2

Cloning of argR Gene and Amplification Effect Thereof in coryneform Bacteria

PCR was performed by using chromosome DNA of the *Brevibacterium flavum* wild strain 2247 (AJ14067) as a template and the oligonucleotides having the nucleotide sequences shown in SEQ ID NO: 15 (sequence of the nucleotide numbers 1717-1741 in SEQ ID NO: 17) and SEQ ID NO: 16 (sequence complementary to the sequence of the nucleotide numbers 2386-2362 in SEQ ID NO: 17) as primers (Primers 15 and 16). PCR was performed for 30 cycles with each cycle consisting of reactions at 98° C. for 10 seconds, 58° C. for 1 minute and 72° C. for 3 minutes by using Pyrobest DNA polymerase (Takara Shuzo Co., Ltd.). The obtained amplified fragment was inserted into the SmaI site of the shuttle vector pSFK6 obtained in Example 1 to obtain plasmid pWR autonomously replicable in coryneform bacteria.

In order to investigate the amplification effect of argR gene in L-arginine producing coryneform bacteria, pWR was introduced into the AJ113455 strain (FERM BP-6894), which is an L-arginine producer of *Brevibacterium flavum*. The plasmid was introduced by the electric pulse method (Japanese Patent Laid-open No. 2-207791). A transformant was selected as a kanamycin resistant strain on CM2G agar medium (containing 5 g of glucose, 5 g of NaCl and 15 g of agar in 1 L of pure water, pH 7.2) containing 25 µg/ml of kanamycin to obtain AJ11345/pWR. As a control, pSFK6 was similarly introduced into the AJ113455 strain to obtain a transformant AJ11345/pSFK6.

Each of the aforementioned strains was plated on an agar medium containing 0.5 g/dl of glucose, 1 g/dl of polypeptone, 1 g/dl of yeast extract and 0.5 g/dl of NaCl, and cultured at 31.5° C. for 20 hours. One platunum loop of the obtained cells were inoculated into a medium containing 4 g/dl of glucose, 6.5 g/dl of ammonium sulfate, 0.1 g/dl of $KH_2PO_4$, 0.04 g/dl of $MgSO_4$, 0.001 g/dl of $FeSO_4$, 0.001 g/dl of $MnSO_4$, 5 µg/dl of vitamin $B_1$, 5 µg/dl of biotin and soybean protein hydrolysate (45 mg/dl as N amount), and cultured in a flask at 31.5° C. for 50 hours with shaking. Accumulation amount of L-arginine (concentration, g/dl) in each culture broth was measured. The results are shown in Table 1. As a result, the argR-amplified strain hardly accumulated L-arginine. This demonstrated that the argR gene product functioned as an arginine repressor.

TABLE 1

| Strain | L-Arginine accumulation amount (g/dl) |
|---|---|
| AJ11345/pSFK6 | 1.3 |
| AJ11345/pWR | 0.2 |

The result of nucleotide sequencing for the inserted fragment cloned in pWR is shown in SEQ ID NO: 17. An amino acid sequence that may be encoded by that nucleotide sequence is shown in SEQ ID NO: 18.

EXAMPLE 3

Construction of argR-Disrupted Strain of coryneform Bacterium and Effect of Deletion of arginine Repressor <1>Construction of plasmid for argR Disruption PCR was performed by using chromosome DNA of a wild strain of *Brevibacterium flavum*, 2247 strain (AJ14067), as a template and the oligonucleotides having the nucleotide sequences shown in SEQ ID NO: 19 (sequence of the nucleotide numbers 4-28 in SEQ ID NO: 17) and SEQ ID NO: 20 (sequence complementary to the sequence of the nucleotide numbers 4230-4211 in SEQ ID NO: 17) as primers (Primers 19 and 20). PCR was performed for 30 cycles with each cycle consisting of reactions at 98° C. for 10 seconds, 58° C. for 1 minute and 72° C. for 3 minutes by using Pyrobest DNA polymerase (Takara Shuzo Co., Ltd.). The obtained amplified fragment was inserted into the SmaI site in a multicloning site of cloning vector pHSG399.

In order to delete the whole ORF considered to encode the arginine repressor from the inserted DNA fragment, PCR was performed by using the oligonucleotides having the nucleotide sequences shown in SEQ ID NO: 21 (sequence of the nucleotide numbers 2372-2395 in SEQ ID NO: 17) and SEQ ID NO: 22 (sequence complementary to the sequence of the nucleotide numbers 1851-1827 in SEQ ID NO: 17) as primers (Primers 21 and 22) and pHSG399 inserted with the amplified fragment as a template. pssER was constructed by self-ligation of the PCR product.

Then, a fragment obtained by digesting pssER with restriction enzymes SmaI and SalI and the temperature sensitive plasmid pSFKT2 obtained in Example 1 and digested with SmaI and SalI were ligated to obtain plasmid pssERT for argR disruption whose autonomous replication ability in coryneform bacteria became temperature sensitive.

<2> Construction of arginine Repressor Deficient Strain of coryneform bacterium by Homologous Recombination The plasmid pssERT obtained as described above was introduced into the *Brevibacterium lactofermentum* AJ13029 strain (FERM BP-5189). The plasmid was introduced by the electric pulse method (Japanese Patent Laid-open No. 2-207791). Because autonomous replication ability of this plasmid is temperature sensitive in *Brevibacterium lactofermentum*, only strains in which this plasmid was incorporated into the chromosome by homologous recombination could be selected as kanamycin resistant strains at 34° C., which was a temperature that did not allow replication of the plasmid. Strains in which the plasmid for argR disruption was incorporated into a chromosome were selected as kanamycin resistant strains on a CM2G plate (containing 10 g/L of polypeptone, 10 g/L of yeast extract, 5 g/L of glucose, 5 g/L of NaCl and 15 g/L of agar in 1 L of water, pH 7.2) containing 25 μg/ml of kanamycin. At this stage, the normal argR gene derived from the chromosome and the argR gene derived from the plasmid in which OFR was deleted were present in tandem at the both sides of the plasmid portion on the chromosome.

Then, the recombinant strains were allowed to cause homologous recombination again, and strains that became kanamycin sensitive at 34° C., which was a temperature that did not allow the plasmid replication, were selected as strains in which one of the argR genes was deleted. These strains include strains in which the normal argR gene remained on the chromosome and strains in which the disrupted argR gene remained on the chromosome. From these strains, a strain having only the disrupted argR gene was selected. An argR gene on the chromosome is determined to be the disrupted type by preparing chromosome of a strain that became kanamycin sensitive at 34° C., performing PCR utilizing the chromosome as a template and the oligonucleotides having the nucleotide sequences shown in SEQ ID NOS: 19 and 20 as primers (Primers 19 and 20), and confirming that the PCR product was shorter by about 600 bp than that obtained by similarly performing PCR utilizing chromosome derived from the parent strain as a template.

Direct sequencing of the PCR product of the argR-disrupted strain selected as described above was performed to confirm that the argR gene was disrupted as desired, and thus AJ13029ΔR stain was obtained. <3>Production of L-arginine with argR-disrupted strain The AJ13029ΔR strain was plated on an agar medium containing 0.5 g/dl of glucose, 1 g/dl of polypeptone, 1 g/dl of yeast extract and 0.5 g/dl of NaCl, and cultured at 31.5° C. for 20 hours. One platinum loop of the obtained cells were inoculated into a medium containing 3 g/dl of glucose, 6.5 g/dl of ammonium sulfate, 0.1 g/dl of $KH_2PO_4$, 0.04 g/dl of $MgSO_4$, 0.001 g/dl of $FeSO_4$, 0.001 g/dl of $MnSO_4$, 300 μg/dl of vitamin $B_1$, 200 μg/dl of biotin and soybean protein hydrolysate (165 mg/dl as N amount) and adjusted to pH 7.0 with NaOH, and cultured at 31.5° C. for 24 hours as seed culture.

The above seed culture broth was. inoculated in an amount of 1 ml into a medium containing 4 g/dl of glucose, 6.5 g/dl of ammonium sulfate, 0.5 g/dl of $KH_2PO_4$, 0.04 g/dl of $MgSO_4$, 0.001 g/dl of $FeSO_4$, 0.01 g/dl of $MnSO_4$, 5 μg/dl of vitamin $B_1$, 5 μg/dl of biotin and soybean protein hydrolysate (45 mg/dl as N amount) and adjusted to pH 7.0 with KOH, and cultured in a flask at 31.5° C. for 50 hours with shaking. Accumulation amount of L-arginine (concentration, mg/dl) in culture broth of each strain was measured. The results are shown in Table 2. As a result, the argR-disrupted strain accumulated L-arginine in a markedly larger amount compared with the parent strain.

TABLE 2

| Strain | L-Arginine accumulation amount (mg/dl) |
|---|---|
| AJ13029 | 20 |
| AJ13029ΔR | 120 |

(Explanation of Sequence Listing)

SEQ ID NO: 1: primer for amplification of kanamycin resistance gene of *Streptococcus faecalis*

SEQ ID NO: 2: primer for amplification of kanamycin resistance gene of *Streptococcus faecalis*

SEQ ID NO: 3: primer for amplification of vector portion of pHSG399

SEQ ID NO: 4: primer for amplification of vector portion of pHSG399

SEQ ID NO: 5: nucleotide sequence of replication control region of pSFK6

SEQ ID NO: 6: amino acid sequence that may be encoded by ORF in pSFK6

SEQ ID NO: 7: nucleotide sequence of replication control region of p48K

SEQ ID NO: 8: amino acid sequence that may be encoded by ORF in p48K

SEQ ID NO: 9: primer for 1st PCR for introducing mutation of 1534th C to T into pSFK6

SEQ ID NO: 10: primer for 1st PCR for introducing mutation of 1534th C to T into pSFK6

SEQ ID NO: 11: primer for 1st PCR for introducing mutation of 1534th C to T into pSFK6

SEQ ID NO: 12: primer for 1st PCR for introducing mutation of 1534th C to T into pSFK6

SEQ ID NO: 13: primer for 2nd PCR for introducing mutation of 1534th C to T into pSFK6

SEQ ID NO: 14: primer for 2nd PCR for introducing mutation of 1534th C to T into pSFK6

SEQ ID NO: 15: primer for argR gene amplification SEQ ID NO: 16: primer for argR gene amplification SEQ ID NO: 17: nucleotide sequence of DNA fragment containing argR gene SEQ ID NO: 18: amino acid sequence that may be encoded by the above DNA fragment SEQ ID NO: 19: primer for argR gene amplification SEQ ID NO: 20: primer for argR gene amplification SEQ ID NO: 21: primer for amplifying portions other than argR gene ORF of plasmid containing argR gene SEQ ID NO: 22: primer for amplifying portions other than argR gene ORF of plasmid containing argR gene

What is claimed is:

1. A method for producing L-arginine, which comprises culturing a coryneform bacterium, in which a polynucleotide encoding the argR arginine repressor on a chromosome of said coryneform bacteruium is disrupted and which has L-arginine producing ability, in a medium to produce and accumulate L-arginine in the medium, and collecting the L-arginine from the medium, wherein said polynucleotide encoding the argR arginine repressor prior to being disrupted is obtained from chromosomal DNA of the coryneform bacterium by PCR with oligonucleotide primers having the nucleotide sequences of SEQ ID NO: 15 and SEQ ID NO: 16 and said coryneform bacterium over produces L-arginine as compared to an unmodified coryneform bacterium.

2. The method of claim 1, wherein said coryneform bacterium belongs to a species selected from the group consisting of Corynebacterium acetoacidophilum,
Corynebacterium acetoglutamicum,
Corynebacterium alkanolyticum,
Corynebacterium callunae,
Corynebacterium glutamicum,
Corynebacterium lilium,
Corynebacterium melassecola,
Corynebacterium thermoaminogenes,
Corynebacterium herculis,
Brevibacterium divaricatum,
Brevibacierium flavum,
Brevibacterium immariophilum,
Brevibacterium lactofermentum,
Brevibacterium roseum,
Brevibacterium saccharolyticum,
Brevibacterium thiogenitalis,
Brevibacterium album,
Brevibacterium cerinum, and
Microbacterium ammoniaphilum.

3. The method of claim 1, wherein said coryneform bacterium is resistant to a compound selected from the group consisting of sulfa drugs, 2-thiazolealanine, and α-amino-β-hydroxyvaleric acid.

4. The method of claim 1, wherein said coryneform bacterium exhibits auxotrophy for a compound selected from the group consisting of L-histidine, L-proline, L-threonine, L-isoleucine, L-methionine, and L-tryptophan.

5. The method of claim 1, wherein said coryneform bacterium is resistant to a compound selected from the group consisting of ketomalonic acid, fluoromalonic acid, and monofluoroacetic acid.

6. The method of claim 1, wherein said coryneform bacterium is resistant to a compound selected from the group consisting of arginol and X-guanidine, wherein X is derived from a fatty acid or aliphatic chain.

7. The method of claim 1, wherein said coryneform bacterium belongs to a genus selected from the group consisting of the genus Corynebacterium, the genus Brevibacterium, and the genus Microbacterium.

8. The method of claim 1, wherein said coryneform bacterium is a recombinant coryneform bacterium.

* * * * *

SEQUENCE LISTING

<160> NUMBER OF SEQ ID NOS: 22

<210> SEQ ID NO 1
<211> LENGTH: 32
<212> TYPE: DNA
<213> ORGANISM: Artificial Sequence
<220> FEATURE:
<223> OTHER INFORMATION: synthetic DNA

<400> SEQUENCE: 1
cccgttaact gcttgaaacc caggacaata ac                32

<210> SEQ ID NO 2
<211> LENGTH: 30
<212> TYPE: DNA
<213> ORGANISM: Artificial Sequence
<220> FEATURE:
<223> OTHER INFORMATION: synthetic DNA

<400> SEQUENCE: 2
cccgttaaca tgtacttcag aaaagattag                  30

<210> SEQ ID NO 3
<211> LENGTH: 26
<212> TYPE: DNA
<213> ORGANISM: Artificial Sequence
<220> FEATURE:
<223> OTHER INFORMATION: synthetic DNA

<400> SEQUENCE: 3
gatatctacg tgccgatcaa cgtctc                      26

<210> SEQ ID NO 4
<211> LENGTH: 25
<212> TYPE: DNA
<213> ORGANISM: Artificial Sequence
<220> FEATURE:
<223> OTHER INFORMATION: synthetic DNA

<400> SEQUENCE: 4
aggccttttt ttaaggcagt tattg                       25

<210> SEQ ID NO 5
<211> LENGTH: 4447
<212> TYPE: DNA
<213> ORGANISM: Brevibacterium lactofermentum
<220> FEATURE:
<221> NAME/KEY: CDS
<222> LOCATION: (1318)..(2598)
<223> OTHER INFORMATION:

<400> SEQUENCE: 5
aagcttgtct acgtctgatg ctttgaatcg gacggacttg ccgatcttgt atgcggtgat     60
ttttccctcg tttgcccact ttttaatggt ggccggggtg agagctacgc gggcggcgac    120
ctgctgcgct gtgatccaat attcggggtc gttcactggt tcccctttct gatttctggc    180
atagaagaac cccgtgaac tgtgtggttc cggggggttgc tgattttttgc gagacttctc    240 gcgcaattcc ctagcttagg tgaaaacacc atgaaacact aggaaacac ccatgaaaca     300 cccattaggg cagtagggcg gcttcttcgt ctagggcttg catttgggcg gtgatctggt    360
ctttagcgtg tgaaagtgtg tcgtaggtgg cgtgctcaat gcactcgaac gtcacgtcat    420
ttaccgggtc acggtgggca aagagaacta gtgggttaga cattgttttc ctcgttgtcg    480

```
gtggtggtga gcttttctag ccgctcggta aacgcggcga tcatgaactc ttggaggttt      540
tcaccgttct gcatgcctgc gcgcttcatg tcctcacgta gtgccaaagg aacgcgtgcg      600
gtgaccacga cgggcttagc ctttgcctgc gcttctagtg cttcgatggt ggcttgtgcc      660
tgcgcttgct gcgcctgtag tgcctgttga gcttcttgta gttgctgttc tagctgtgcc      720
ttggttgcca tgctttaaga ctctagtagc tttcctgcga tatgtcatgc gcatgcgtag      780
caaacattgt cctgcaactc attcattatg tgcagtgctc ctgttactag tcgtacatac      840
tcatatttac ctagtctgca tgcagtgcat gcacatgcag tcatgtcgtg ctaatgtgta      900
aaacatgtac atgcagattg ctgggggtgc aggggcgga gccaccctgt ccatgcgggg       960 tgtgggggctt gccccgccgg tacagacagt gagcaccggg gcacctagtc gcggataccc    1020
cccctaggta tcggacacgt aaccctccca tgtcgatgca aatctttaac attgagtacg    1080
ggtaagctgg cacgcatagc caagctaggc ggccaccaaa caccactaaa aattaatagt    1140
ccctagacaa gacaaacccc cgtgcgagct accaactcat atgcacgggg gccacataac    1200
ccgaaggggt ttcaattgac aaccatagca ctagctaaga caacgggcac aacacccgca    1260
caaactcgca ctgcgcaacc ccgcacaaca tcgggtctag gtaacactga aatagaa       1317 gtg aac acc tct aag gaa ccg cag gtc aat gag ggt tct aag gtc act       1365
Val Asn Thr Ser Lys Glu Pro Gln Val Asn Glu Gly Ser Lys Val Thr
1               5                   10                  15 cgc gct agg gcg tgg cgt agg caa aac gtc atg tac aag atc acc aat       1413
Arg Ala Arg Ala Trp Arg Arg Gln Asn Val Met Tyr Lys Ile Thr Asn
            20                  25                  30 agt aag gct ctg gcg ggg tgc cat agg tgg cgc agg gac gaa gct gtt       1461
Ser Lys Ala Leu Ala Gly Cys His Arg Trp Arg Arg Asp Glu Ala Val
        35                  40                  45 gcg gtg tcc tgg tcg tct aac ggt gct tcg cag ttt gag ggt ctg caa       1509
Ala Val Ser Trp Ser Ser Asn Gly Ala Ser Gln Phe Glu Gly Leu Gln
    50                  55                  60 aac tct cac tct cgc tgg ggg tca cct ctg gct gaa ttg gaa gtc atg       1557
Asn Ser His Ser Arg Trp Gly Ser Pro Leu Ala Glu Leu Glu Val Met
65                  70                  75                  80 ggc gaa cgc cgc att gag ctg gct att gct act aag aat cac ttg gcg       1605
Gly Glu Arg Arg Ile Glu Leu Ala Ile Ala Thr Lys Asn His Leu Ala
                85                  90                  95 gcg ggt ggc gcg ctc atg atg ttt gtg ggc act gtt cga cac aac cgc       1653
Ala Gly Gly Ala Leu Met Met Phe Val Gly Thr Val Arg His Asn Arg
            100                 105                 110 tca cag tca ttt gcg cag gtt gaa gcg ggt att aag act gcg tac tct       1701
Ser Gln Ser Phe Ala Gln Val Glu Ala Gly Ile Lys Thr Ala Tyr Ser
        115                 120                 125 tcg atg gtg aaa aca tct cag tgg aag aaa gaa cgt gca cgg tac ggg       1749
Ser Met Val Lys Thr Ser Gln Trp Lys Lys Glu Arg Ala Arg Tyr Gly
    130                 135                 140 gtg gag cac acc tat agt gac tat gag gtc aca gac tct tgg gcg aac       1797
Val Glu His Thr Tyr Ser Asp Tyr Glu Val Thr Asp Ser Trp Ala Asn
145                 150                 155                 160 ggt tgg cac ttg cac cgc aac atg ctg ttg ttc ttg gat cgt cca ctg       1845
Gly Trp His Leu His Arg Asn Met Leu Leu Phe Leu Asp Arg Pro Leu
                165                 170                 175 tct gac gat gaa ctc aag gcg ttt gag gat tcc atg ttt tcc cgc tgg       1893
Ser Asp Asp Glu Leu Lys Ala Phe Glu Asp Ser Met Phe Ser Arg Trp
            180                 185                 190 tct gct ggt gtg gtt aag gcc ggt atg gac gcg cca ctg cgt gag cac       1941
Ser Ala Gly Val Val Lys Ala Gly Met Asp Ala Pro Leu Arg Glu His
```

-continued

```
               195                 200                 205
ggg gtc aaa ctt gat cag gtg tct acc tgg ggt gga gac gct gcg aaa       1989
Gly Val Lys Leu Asp Gln Val Ser Thr Trp Gly Gly Asp Ala Ala Lys
    210                 215                 220 atg gca acc tac ctc gct aag ggc atg tct cag gaa ctg act ggc tcc       2037
Met Ala Thr Tyr Leu Ala Lys Gly Met Ser Gln Glu Leu Thr Gly Ser
225                 230                 235                 240 gct act aaa acc gcg tct aag ggg tcg tac acg ccg ttt cag atg ttg       2085
Ala Thr Lys Thr Ala Ser Lys Gly Ser Tyr Thr Pro Phe Gln Met Leu
                245                 250                 255 gat atg ttg gcc gat caa agc gac gcc ggc gag gat atg gac gct gtt       2133
Asp Met Leu Ala Asp Gln Ser Asp Ala Gly Glu Asp Met Asp Ala Val
            260                 265                 270 ttg gtg gct cgg tgg cgt gag tat gag gtt ggt tct aaa aac ctg cgt       2181
Leu Val Ala Arg Trp Arg Glu Tyr Glu Val Gly Ser Lys Asn Leu Arg
        275                 280                 285 tcg tcc tgg tca cgt ggg gct aag cgt gct ttg ggc att gat tac ata       2229
Ser Ser Trp Ser Arg Gly Ala Lys Arg Ala Leu Gly Ile Asp Tyr Ile
    290                 295                 300 gac gct gat gta cgt cgt gaa atg gaa gaa gaa ctg tac aag ctc gcc       2277
Asp Ala Asp Val Arg Arg Glu Met Glu Glu Glu Leu Tyr Lys Leu Ala
305                 310                 315                 320 ggt ctg gaa gca ccg gaa cgg gtc gaa tca acc cgc gtt gct gtt gct       2325
Gly Leu Glu Ala Pro Glu Arg Val Glu Ser Thr Arg Val Ala Val Ala
                325                 330                 335 ttg gtg aag ccc gat gat tgg aaa ctg att cag tct gat ttc gcg gtt       2373
Leu Val Lys Pro Asp Asp Trp Lys Leu Ile Gln Ser Asp Phe Ala Val
            340                 345                 350 agg cag tac gtt cta gat tgc gtg gat aag gct aag gac gtg gcc gct       2421
Arg Gln Tyr Val Leu Asp Cys Val Asp Lys Ala Lys Asp Val Ala Ala
        355                 360                 365 gcg caa cgt gtc gct aat gag gtg ctg gca agt ctg ggt gtg gat tcc       2469
Ala Gln Arg Val Ala Asn Glu Val Leu Ala Ser Leu Gly Val Asp Ser
    370                 375                 380 acc ccg tgc atg atc gtt atg gat gat gtg gac ttg gac gcg gtt ctg       2517
Thr Pro Cys Met Ile Val Met Asp Asp Val Asp Leu Asp Ala Val Leu
385                 390                 395                 400 cct act cat ggg gac gct act aag cgt gat ctg aat gcg gcg gtg ttc       2565
Pro Thr His Gly Asp Ala Thr Lys Arg Asp Leu Asn Ala Ala Val Phe
                405                 410                 415 gcg ggt aat gag cag act att ctt cgc acc cac taaaagcggc ataaaccccg    2618
Ala Gly Asn Glu Gln Thr Ile Leu Arg Thr His
            420                 425 ttcgatattt tgtgcgatga atttatggtc aatgtcgcgg gggcaaacta tgatgggtct    2678
tgttgttgac aatggctgat ttcatcagga atggaactgt catgctgtta tgtgcctggc    2738
tcctaatcaa agctggggac aatgggttgc cccgttgatc tgatctagtt cggattggcg    2798
gggcttcact gtatctgggg gtggcatcgt gaatagattg cacaccgtag tgggcagtgt    2858
gcacaccata gtgggcatga gtaataccta cgcgcgcgtg ggctagggct taacgcgcgt    2918
tttgccgtgc tgcggggcat acgttagcgc atacgctttt ttctgtgaaa ccttttttgtg    2978 ttgttgtttc gtgttggttt cctttctgtt ggcggggcaa cttaacgcct gcggggtgg    3038 ttgttgacgt taacggggt agttttattt cccctagtgg ttttttcagta cgacaatcga    3098 gaaagacctg tttcagccag ttcgggtcat gttcgtcggt atggccacgt gcatagcgac    3158
cagttttcga gttcactggg atttttggtg catcgaacaa gatgtaggac aatgcgggttt   3218 ctaggtctac ttttttgctttt atgccgtaca agccccgtgg gtattcagcg attgattcca    3278
```

-continued

```
aggcggcttc ccagtcctgt tttgtgaagg actggcttag ttctaggtct gtgtctgggt      3338
agtactgctt gtttgtgtaa gcgccgttgg tgctcattga tgattccttt gaagtgtttg      3398
gagttcggct agtagtgcgg cgtatggtgc tgcttttgc tcgtgatagc tcgccttggc       3458
tatgaggtcg gctaggtagg tttccggggt gcctaggttg cgtaggtcta gcaaatcccg      3518
gtatgtggcc tgtgcgctgc gctggtggtg catacagtcg ttaagctggg cttttacgtc      3578
tgcgatgcgg tggcggttag gcatgttggt gtgcttcttc caagtactca cgggcgggtt     3638
ttgtgtatgc ctggcgtgat gcttctttga gctgttggag ttccgcttgg agtgcgggta     3698
gttcgtccgc gaactgcttg tggtactcgt atttctcttg ttcctgggcg atagcatttg     3758
cgttgaattg cagggcggtg agttcgtcca cgcgtcgttt tgctgcgttg gtcatggtgg    3818
cgtgccattt gcggttgtgg acgcggggtt caaggttgcg cacggctgct tcggctaggt    3878
tggtggctgc ttttttcagt gctcgggctt cccgttcctc gtccaacgag agcacctttg    3938
gtttgttggc ttcggctagt ttttgcttct ccgctttgat gagttggtca acttcgtgtt    3998
gggagaggtc gttttttcacg atgcgtcgaa tgtggtcgtt gtgggtgctg agttggtgtg    4058
agaggtagtg gggttctggg atttcggcga gttggtcgag gttggtgtag tgcgggttgc    4118
ggcctggttg gttgggttcg ctggggaggt cgatgtatcc ggttgagtct ccggcgtggt    4178
tgaagtgaat taggcgttgg tagccgtatt cctggttggg gaggtacgac agaatgagga    4238
agtttggtgc ttctcctgca atgagtcgtg cgtgttcgta gttcggtact gggtcgtgct    4298
cggggagaat gttcttttgg gtcatggctt ctctttctgt tgctctgtaa gtccgtatgt    4358
gggcatggga aagccccggc aacccttggg gtcaaccggg gctagatagt cgcttagaat    4418
ggcttctagg ctgcgtctcg gggtgtggc                                       4447
```

<210> SEQ ID NO 6
<211> LENGTH: 427
<212> TYPE: PRT
<213> ORGANISM: Brevibacterium lactofermentum

<400> SEQUENCE: 6

```
Val Asn Thr Ser Lys Glu Pro Gln Val Asn Glu Gly Ser Lys Val Thr
1               5                   10                  15

Arg Ala Arg Ala Trp Arg Arg Gln Asn Val Met Tyr Lys Ile Thr Asn
            20                  25                  30

Ser Lys Ala Leu Ala Gly Cys His Arg Trp Arg Arg Asp Glu Ala Val
        35                  40                  45

Ala Val Ser Trp Ser Ser Asn Gly Ala Ser Gln Phe Glu Gly Leu Gln
    50                  55                  60

Asn Ser His Ser Arg Trp Gly Ser Pro Leu Ala Glu Leu Glu Val Met
65                  70                  75                  80

Gly Glu Arg Arg Ile Glu Leu Ala Ile Ala Thr Lys Asn His Leu Ala
                85                  90                  95

Ala Gly Gly Ala Leu Met Met Phe Val Gly Thr Val Arg His Asn Arg
            100                 105                 110

Ser Gln Ser Phe Ala Gln Val Glu Ala Gly Ile Lys Thr Ala Tyr Ser
        115                 120                 125

Ser Met Val Lys Thr Ser Gln Trp Lys Lys Glu Arg Ala Arg Tyr Gly
    130                 135                 140

Val Glu His Thr Tyr Ser Asp Tyr Glu Val Thr Asp Ser Trp Ala Asn
145                 150                 155                 160
```

```
Gly Trp His Leu His Arg Asn Met Leu Leu Phe Leu Asp Arg Pro Leu
                165                 170                 175
Ser Asp Asp Glu Leu Lys Ala Phe Glu Asp Ser Met Phe Ser Arg Trp
            180                 185                 190
Ser Ala Gly Val Val Lys Ala Gly Met Asp Ala Pro Leu Arg Glu His
        195                 200                 205
Gly Val Lys Leu Asp Gln Val Ser Thr Trp Gly Gly Asp Ala Ala Lys
    210                 215                 220
Met Ala Thr Tyr Leu Ala Lys Gly Met Ser Gln Glu Leu Thr Gly Ser
225                 230                 235                 240
Ala Thr Lys Thr Ala Ser Lys Gly Ser Tyr Thr Pro Phe Gln Met Leu
                245                 250                 255
Asp Met Leu Ala Asp Gln Ser Asp Ala Gly Glu Asp Met Asp Ala Val
            260                 265                 270
Leu Val Ala Arg Trp Arg Glu Tyr Glu Val Gly Ser Lys Asn Leu Arg
        275                 280                 285
Ser Ser Trp Ser Arg Gly Ala Lys Arg Ala Leu Gly Ile Asp Tyr Ile
    290                 295                 300
Asp Ala Asp Val Arg Arg Glu Met Glu Glu Leu Tyr Lys Leu Ala
305                 310                 315                 320
Gly Leu Glu Ala Pro Glu Arg Val Glu Ser Thr Arg Val Ala Val Ala
                325                 330                 335
Leu Val Lys Pro Asp Asp Trp Lys Leu Ile Gln Ser Asp Phe Ala Val
            340                 345                 350
Arg Gln Tyr Val Leu Asp Cys Val Asp Lys Ala Lys Asp Val Ala Ala
        355                 360                 365
Ala Gln Arg Val Ala Asn Glu Val Leu Ala Ser Leu Gly Val Asp Ser
    370                 375                 380
Thr Pro Cys Met Ile Val Met Asp Asp Val Asp Leu Asp Ala Val Leu
385                 390                 395                 400
Pro Thr His Gly Asp Ala Thr Lys Arg Asp Leu Asn Ala Ala Val Phe
                405                 410                 415
Ala Gly Asn Glu Gln Thr Ile Leu Arg Thr His
                420                 425

<210> SEQ ID NO 7
<211> LENGTH: 4447
<212> TYPE: DNA
<213> ORGANISM: Brevibacterium lactofermentum
<220> FEATURE:
<221> NAME/KEY: CDS
<222> LOCATION: (1318)..(2598)
<223> OTHER INFORMATION:

<400> SEQUENCE: 7
aagcttgtct acgtctgatg ctttgaatcg gacggacttg ccgatcttgt atgcggtgat      60
ttttccctcg tttgcccact ttttaatggt ggccggggtg agagctacgc gggcggcgac     120
ctgctgcgct gtgatccaat attcggggtc gttcactggt tcccctttct gatttctggc     180
atagaagaac ccccgtgaac tgtgtggttc cgggggttgc tgattttttgc gagacttctc    240 gcgcaattcc ctagcttagg tgaaaacacc atgaaacact agggaaacac ccatgaaaca    300
cccattaggg cagtagggcg gcttcttcgt ctagggcttg catttgggcg gtgatctggt    360
ctttagcgtg tgaaagtgtg tcgtaggtgg cgtgctcaat gcactcgaac gtcacgtcat    420
ttaccgggtc acggtgggca aagagaacta gtgggttaga cattgttttc ctcgttgtcg    480
```

-continued

```
gtggtggtga gcttttctag ccgctcggta aacgcggcga tcatgaactc ttggaggttt    540
tcaccgttct gcatgcctgc gcgcttcatg tcctcacgta gtgccaaagg aacgcgtgcg    600
gtgaccacga cgggcttagc ctttgcctgc gcttctagtg cttcgatggt ggcttgtgcc    660
tgcgcttgct gcgcctgtag tgcctgttga gcttcttgta gttgctgttc tagctgtgcc    720
ttggttgcca tgctttaaga ctctagtagc tttcctgcga tatgtcatgc gcatgcgtag    780
caaacattgt cctgcaactc attcattatg tgcagtgctc ctgttactag tcgtacatac    840
tcatatttac ctagtctgca tgcagtgcat gcacatgcag tcatgtcgtg ctaatgtgta    900
aaacatgtac atgcagattg ctgggggtgc aggggcgga gccaccctgt ccatgcgggg    960
tgtgggctt gccccgccgg tacagacagt gagcaccggg gcacctagtc gcggataccc    1020
cccctaggta tcgacacgt aaccctccca tgtcgatgca atctttaac attgagtacg    1080
ggtaagctgg cacgcatagc caagctaggc ggccaccaaa caccactaaa aattaatagt    1140
tcctagacaa gacaaacccc cgtgcgagct accaactcat atgcacgggg gccacataac    1200
ccgaaggggt ttcaattgac aaccatagca ctagctaaga caacgggcac aacatccgca    1260
caaactcgca ctgcgcaacc ccgcacaaca tcgggtctag gtaacactga aatagaa      1317 gtg aac acc tct aag gaa ccg cag gtc aat gag ggt tct aag gtc act    1365
Val Asn Thr Ser Lys Glu Pro Gln Val Asn Glu Gly Ser Lys Val Thr
  1               5                  10                  15 cgc gct agg gcg tgg cgt agg caa aac gtc atg tac aag atc acc aat    1413
Arg Ala Arg Ala Trp Arg Arg Gln Asn Val Met Tyr Lys Ile Thr Asn
             20                  25                  30 agt aag gct ctg gcg ggg tgc cat agg tgg cgc agg gac gaa gct gtt    1461
Ser Lys Ala Leu Ala Gly Cys His Arg Trp Arg Arg Asp Glu Ala Val
         35                  40                  45 gcg gtg tcc tgg tcg tct aac ggt gct tcg cag ttt gag ggt ctg caa    1509
Ala Val Ser Trp Ser Ser Asn Gly Ala Ser Gln Phe Glu Gly Leu Gln
     50                  55                  60 aac tct cac tct cgc tgg ggg tca tct ctg gct gaa ttg gaa gtc atg    1557
Asn Ser His Ser Arg Trp Gly Ser Ser Leu Ala Glu Leu Glu Val Met
 65                  70                  75                  80 ggc gaa cgc cgc att gag ctg gct att gct act aag aat cac ttg gcg    1605
Gly Glu Arg Arg Ile Glu Leu Ala Ile Ala Thr Lys Asn His Leu Ala
                 85                  90                  95 gcg ggt ggc gcg ctc atg atg ttt gtg ggc act gtt cga cac aac cgc    1653
Ala Gly Gly Ala Leu Met Met Phe Val Gly Thr Val Arg His Asn Arg
            100                 105                 110 tca cag tca ttt gcg cag gtt gaa gcg ggt att aag act gcg tac tct    1701
Ser Gln Ser Phe Ala Gln Val Glu Ala Gly Ile Lys Thr Ala Tyr Ser
        115                 120                 125 tcg atg gtg aaa aca tct cag tgg aag aaa gaa cgt gca cgg tac ggg    1749
Ser Met Val Lys Thr Ser Gln Trp Lys Lys Glu Arg Ala Arg Tyr Gly
    130                 135                 140 gtg gag cac acc tat agt gac tat gag gtc aca gac tct tgg gcg aac    1797
Val Glu His Thr Tyr Ser Asp Tyr Glu Val Thr Asp Ser Trp Ala Asn
145                 150                 155                 160 ggt tgg cac ttg cac cgc aac atg ctg ttg ttc ttg gat cgt cca ctg    1845
Gly Trp His Leu His Arg Asn Met Leu Leu Phe Leu Asp Arg Pro Leu
                165                 170                 175 tct gac gat gaa ctc aag gca ttt gag gat tcc atg ttt tcc cgc tgg    1893
Ser Asp Asp Glu Leu Lys Ala Phe Glu Asp Ser Met Phe Ser Arg Trp
            180                 185                 190 tct gct ggt gtg gtt aag gcc ggt atg gac gcg cca ctg cgt gag cac    1941
Ser Ala Gly Val Val Lys Ala Gly Met Asp Ala Pro Leu Arg Glu His
        195                 200                 205
```

| | | | | | | | | | | | | |
|---|---|---|---|---|---|---|---|---|---|---|---|---|
| ggg | gtc | aaa | ctt | gat | cag | gtg | tct | acc | tgg | ggt | gga | gac | gct | gcg | aaa | 1989 |
| Gly | Val | Lys | Leu | Asp | Gln | Val | Ser | Thr | Trp | Gly | Gly | Asp | Ala | Ala | Lys | |
| 210 | | | | | 215 | | | | | 220 | | | | | | |

```
ggg gtc aaa ctt gat cag gtg tct acc tgg ggt gga gac gct gcg aaa    1989
Gly Val Lys Leu Asp Gln Val Ser Thr Trp Gly Gly Asp Ala Ala Lys
            210             215             220 atg gca acc tac ctc gct aag ggc atg tct cag gaa ctg act ggc tcc    2037
Met Ala Thr Tyr Leu Ala Lys Gly Met Ser Gln Glu Leu Thr Gly Ser
225             230             235             240 gct act aaa acc gcg tct aaa ggg tcg tac acg ccg ttt cag atg ttg    2085
Ala Thr Lys Thr Ala Ser Lys Gly Ser Tyr Thr Pro Phe Gln Met Leu
            245             250             255 gat atg ttg gcc gat caa agc gac gcc ggc gag gat atg gac gct gtt    2133
Asp Met Leu Ala Asp Gln Ser Asp Ala Gly Glu Asp Met Asp Ala Val
260             265             270 ttg gtg gct cgg tgg cgt gag tat gag gtt ggt tct aaa aac ctg cgt    2181
Leu Val Ala Arg Trp Arg Glu Tyr Glu Val Gly Ser Lys Asn Leu Arg
            275             280             285 tcg tct tgg tca cgt ggg gct aag cgt gct ttg ggc att gat tac ata    2229
Ser Ser Trp Ser Arg Gly Ala Lys Arg Ala Leu Gly Ile Asp Tyr Ile
290             295             300 gac gct gat gta cgt cgt gaa atg gaa gaa gaa ctg tac aag ctc gcc    2277
Asp Ala Asp Val Arg Arg Glu Met Glu Glu Glu Leu Tyr Lys Leu Ala
305             310             315             320 ggt ctg gaa gca ccg gaa cgg gtc gaa tca acc cgc gtt gct gtt gct    2325
Gly Leu Glu Ala Pro Glu Arg Val Glu Ser Thr Arg Val Ala Val Ala
            325             330             335 ttg gtg aag ccc gat gat tgg aaa ctg att cag tct gat ttc gcg gtt    2373
Leu Val Lys Pro Asp Asp Trp Lys Leu Ile Gln Ser Asp Phe Ala Val
340             345             350 agg cag tac gtt cta gat tgc gtg gat aag gct aag gac gtg gcc gct    2421
Arg Gln Tyr Val Leu Asp Cys Val Asp Lys Ala Lys Asp Val Ala Ala
            355             360             365 gcg caa cgt gtc gct aat gag gtg ctg gca agt ctg ggt gtg gat tcc    2469
Ala Gln Arg Val Ala Asn Glu Val Leu Ala Ser Leu Gly Val Asp Ser
370             375             380 acc ccg tgc atg atc gtt atg gat gat gtg gac ttg gac gcg gtt ctg    2517
Thr Pro Cys Met Ile Val Met Asp Asp Val Asp Leu Asp Ala Val Leu
385             390             395             400 cct act cat ggg gac gct act aag cgt gat ctg aat gcg gcg gtg ttc    2565
Pro Thr His Gly Asp Ala Thr Lys Arg Asp Leu Asn Ala Ala Val Phe
            405             410             415 gcg ggt aat gag cag act att ctt cgc acc cac taaaagcggc ataaaccccg  2618
Ala Gly Asn Glu Gln Thr Ile Leu Arg Thr His
            420             425 ttcgatattt tgtgcgatga atttatggtc aatgtcgcgg gggcaaacta tgatgggtct  2678
tgttgttgac aatggctgat ttcatcagga atggaactgt catgctgtta tgtgcctggc  2738
tcctaatcaa agctggggac aatgggttgc cccgttgatc tgatctagtt cggattggcg  2798
gggcttcact gtatctgggg gtggcatcgt gaatagattg cacaccgtag tgggcagtgt  2858
gcacaccata gtgggcatga gtaataccta cgcgcgcgtg ggctagggct taacgcgcgt  2918
tttgccgtgc tgcggggcat acgttagcgc atacgctttt ttctgtgaaa ccttttttgtg  2978 ttgttgtttc gtgttggttt cctttctgtt ggcggggcaa cttaacgcct gcggggtgg   3038 ttgttgacgt taacggggt agttttatt cccctagtgg tttttcagta cgacaatcga   3098
gaaagacctg tttcagccag ttcgggtcat gttcgtcggt atggcacgt gcatagcgac   3158 cagttttcga gttcactggg attttggtg catcaaacaa gatgtaggac aatgcggttt   3218
ctaggtctac ttttttgcttt atgccgtaca agccccgtgg gtattcagcg attgattcca   3278
```

-continued

```
aggcggcttc ccagtcctgt tttgtgaagg actggcttag ttctaggtct gtgtctgggt    3338
agtactgctt gtttgtgtaa gcgccgttgg tgctcattga tgattccttt gaagtgtttg    3398
gagttcggct agtagtgcgg cgtatgtgtc tgcttttgc tcgtgatagc tcgccttggc     3458
tatgaggtcg gctaggtagg tttccggggt gcctaggttg cgtaggtcta gcaaatcccg    3518
gtatgtggcc tgtgcgctgc gctggtggtg catacagtcg ttaagctggg cttttacgtc    3578
tgcgatgcgg tggcggttag gcatgttggt gtgcttcttc caagtactca cgggcgggtt    3638
ttgtgtatgc ctggcgtgat gcttctttga gctgttggag ttccgcttgg agtgcgggta    3698
gttcgtccgc gaactgcttg tggtactcgt atttctcttg ttcctgggcg atagcatttg    3758
cgttgaattg cagggcggtg agttcgtcca cgcgtcgttt tgctgcgttg gtcatggtgg    3818
cgtgccattt gcggttgtgg acgcggggtt caaggttgcg cacggctgct tcggctaggt    3878
tggtggctgc ttttttcagt gctcgggctt cccgttcctc gtccaacgag agcacctttg    3938
gtttgttggc ttcggctagt ttttgcttct ccgctttgat gagttggtca acttcgtgtt    3998
gggagaggtc gttttcacg atgcgtcgaa tgtggtcgtt gtgggtgctg agttggtgtg      4058
agaggtagtg gggttctggg atttcggcga gttggtcgag gttggtgtag tgcgggttgc    4118
ggcctggttg gttgggttcg ctggggaggt cgatgtatcc ggttgagtct ccggcgtggt    4178
tgaagtgaat taggcgttgg tagccgtatt cctggttggg gaggtacgac agaatgagga    4238
agtttggtgc ttctcctgca atgagtcgtg cgtgttcgta gttcggtact gggtcgtgct    4298
cggggagaat gttcttttgg gtcatggctt ctctttctgt tgctctgtaa gtccgtatgt    4358
gggcatggga aagccccggc aaccctttgg gtcaaccggg gctagatagt cgcttagaat    4418
ggcttctagg ctgcgtctcg ggtgtggc                                        4447
```

<210> SEQ ID NO 8
<211> LENGTH: 427
<212> TYPE: PRT
<213> ORGANISM: Brevibacterium lactofermentum

<400> SEQUENCE: 8

```
Val Asn Thr Ser Lys Glu Pro Gln Val Asn Glu Gly Ser Lys Val Thr
 1               5                  10                  15

Arg Ala Arg Ala Trp Arg Arg Gln Asn Val Met Tyr Lys Ile Thr Asn
            20                  25                  30

Ser Lys Ala Leu Ala Gly Cys His Arg Trp Arg Arg Asp Glu Ala Val
        35                  40                  45

Ala Val Ser Trp Ser Ser Asn Gly Ala Ser Gln Phe Glu Gly Leu Gln
    50                  55                  60

Asn Ser His Ser Arg Trp Gly Ser Ser Leu Ala Glu Leu Glu Val Met
65                  70                  75                  80

Gly Glu Arg Arg Ile Glu Leu Ala Ile Ala Thr Lys Asn His Leu Ala
                85                  90                  95

Ala Gly Gly Ala Leu Met Met Phe Val Gly Thr Val Arg His Asn Arg
            100                 105                 110

Ser Gln Ser Phe Ala Gln Val Glu Ala Gly Ile Lys Thr Ala Tyr Ser
        115                 120                 125

Ser Met Val Lys Thr Ser Gln Trp Lys Lys Glu Arg Ala Arg Tyr Gly
    130                 135                 140

Val Glu His Thr Tyr Ser Asp Tyr Glu Val Thr Asp Ser Trp Ala Asn
145                 150                 155                 160

Gly Trp His Leu His Arg Asn Met Leu Leu Phe Leu Asp Arg Pro Leu
```

-continued

```
                    165                 170                 175
Ser Asp Asp Glu Leu Lys Ala Phe Glu Asp Ser Met Phe Ser Arg Trp
            180                 185                 190

Ser Ala Gly Val Val Lys Ala Gly Met Asp Ala Pro Leu Arg Glu His
        195                 200                 205

Gly Val Lys Leu Asp Gln Val Ser Thr Trp Gly Gly Asp Ala Ala Lys
    210                 215                 220

Met Ala Thr Tyr Leu Ala Lys Gly Met Ser Gln Glu Leu Thr Gly Ser
225                 230                 235                 240

Ala Thr Lys Thr Ala Ser Lys Gly Ser Tyr Thr Pro Phe Gln Met Leu
                245                 250                 255

Asp Met Leu Ala Asp Gln Ser Asp Ala Gly Glu Asp Met Asp Ala Val
            260                 265                 270

Leu Val Ala Arg Trp Arg Glu Tyr Glu Val Gly Ser Lys Asn Leu Arg
        275                 280                 285

Ser Ser Trp Ser Arg Gly Ala Lys Arg Ala Leu Gly Ile Asp Tyr Ile
    290                 295                 300

Asp Ala Asp Val Arg Arg Glu Met Glu Glu Leu Tyr Lys Leu Ala
305                 310                 315                 320

Gly Leu Glu Ala Pro Glu Arg Val Glu Ser Thr Arg Val Ala Val Ala
                325                 330                 335

Leu Val Lys Pro Asp Asp Trp Lys Leu Ile Gln Ser Asp Phe Ala Val
            340                 345                 350

Arg Gln Tyr Val Leu Asp Cys Val Asp Lys Ala Lys Asp Val Ala Ala
        355                 360                 365

Ala Gln Arg Val Ala Asn Glu Val Leu Ala Ser Leu Gly Val Asp Ser
    370                 375                 380

Thr Pro Cys Met Ile Val Met Asp Asp Val Asp Leu Asp Ala Val Leu
385                 390                 395                 400

Pro Thr His Gly Asp Ala Thr Lys Arg Asp Leu Asn Ala Ala Val Phe
                405                 410                 415

Ala Gly Asn Glu Gln Thr Ile Leu Arg Thr His
            420                 425

<210> SEQ ID NO 9
<211> LENGTH: 30
<212> TYPE: DNA
<213> ORGANISM: Artificial Sequence
<220> FEATURE:
<223> OTHER INFORMATION: synthetic DNA

<400> SEQUENCE: 9
aaacccgggc tacgtctgat gctttgaatc                                      30

<210> SEQ ID NO 10
<211> LENGTH: 27
<212> TYPE: DNA
<213> ORGANISM: Artificial Sequence
<220> FEATURE:
<223> OTHER INFORMATION: synthetic DNA

<400> SEQUENCE: 10
tttgatcccc cgttaacgtc aacaacc                                         27

<210> SEQ ID NO 11
<211> LENGTH: 28
<212> TYPE: DNA
<213> ORGANISM: Artificial Sequence
```

```
<220> FEATURE:
<223> OTHER INFORMATION: synthetic DNA

<400> SEQUENCE: 11
ttttcccggg agcttgccac accccgag                                              28

<210> SEQ ID NO 12
<211> LENGTH: 24
<212> TYPE: DNA
<213> ORGANISM: Artificial Sequence
<220> FEATURE:
<223> OTHER INFORMATION: synthetic DNA

<400> SEQUENCE: 12
gggggtcatc tctggctgaa ttgg                                                  24

<210> SEQ ID NO 13
<211> LENGTH: 24
<212> TYPE: DNA
<213> ORGANISM: Artificial Sequence
<220> FEATURE:
<223> OTHER INFORMATION: synthetic DNA

<400> SEQUENCE: 13
gaggttttca ccgttctgca tgcc                                                  24

<210> SEQ ID NO 14
<211> LENGTH: 23
<212> TYPE: DNA
<213> ORGANISM: Artificial Sequence
<220> FEATURE:
<223> OTHER INFORMATION: synthetic DNA

<400> SEQUENCE: 14
aactcaccgc cctgcaattc aac                                                   23

<210> SEQ ID NO 15
<211> LENGTH: 25
<212> TYPE: DNA
<213> ORGANISM: Artificial Sequence
<220> FEATURE:
<223> OTHER INFORMATION: synthetic DNA

<400> SEQUENCE: 15
gcctaccgcg gcaaagaagt ggcag                                                 25

<210> SEQ ID NO 16
<211> LENGTH: 25
<212> TYPE: DNA
<213> ORGANISM: Artificial Sequence
<220> FEATURE:
<223> OTHER INFORMATION: synthetic DNA

<400> SEQUENCE: 16
gccttgaact aggggcgctt taagt                                                 25

<210> SEQ ID NO 17
<211> LENGTH: 4235
<212> TYPE: DNA
<213> ORGANISM: Brevibacterium flavum
<220> FEATURE:
<221> NAME/KEY: CDS
<222> LOCATION: (1852)..(2364)
<223> OTHER INFORMATION:

<400> SEQUENCE: 17
```

```
aaacccgggt tttcttctgc aactcgggcg ccgaagcaaa cgaggctgct ttcaagattg    60
cacgcttgac tggtcgttcc cggattctgg ctgcagttca tggtttccac ggccgcacca   120
tgggttccct cgcgctgact ggccagccag acaagcgtga agcgttcctg ccaatgccaa   180
gcggtgtgga gttctaccct tacggcgaca ccgattactt gcgcaaaatg gtagaaacca   240
acccaacgga tgtggctgct atcttcctcg agccaatcca gggtgaaacg ggcgttgttc   300
cagcacctga aggattcctc aaggcagtgc gcgagctgtg cgatgagtac ggcatcttga   360
tgatcaccga tgaagtccag actggcgttg gccgtaccgg cgatttcttt gcacatcagc   420
acgatggcgt tgttcccgat gtggtgacca tggccaaggg acttggcggc ggtcttccca   480
tcggtgcttg tttggccact ggccgtgcag ctgaattgat daccccaggc aagcacggca   540
ccactttcgg tggcaaccca gttgcttgtg cagctgccaa ggcagtgctg tctgttgtcg   600
atgacgcttt ctgcgcagaa gttacccgca agggcgagct gttcaaggta cttcttgcca   660
aggttgacgg cgttgtagac gtccgtggca ggggcttgat gttgggcgtg gtgctggagc   720
gcgacgtcgc aaagcaagct gttcttgatg gttttaagca cggcgttatt ttgaatgcac   780
cggcggacaa cattatccgt ttgaccccgc cgctggtgat caccgacgaa gaaatcgcag   840
acgcagtcaa ggctattgcc gagacaatcg cataaaggac ttaaacttat gacttcacaa   900
ccacaggttc gccatttcct ggctgatgat gatctcaccc ctgcagagca ggcagaggtt   960
ttgaccctag ccgcaaagct caaggcagcg ccgttttcgg agcgtccact cgagggacca  1020
aagtccgttg cagttctttt tgataagact tcaactcgta ctcgcttctc cttcgacgcg  1080
ggcatcgctc atttgggtgg acatgccatc gtcgtggatt ccggcagctc acagatgggt  1140
aagggcgaga ccctgcagga caccgcagct gtattgtccc gctacgtgga agcaattgtg  1200
tggcgcacct acgcacacag caatttccac gccatggcgg agacgtccac tgtgccgctg  1260
gtgaactcct tgtccgatga tctgcaccca tgccagattc tggctgatct gcagaccatc  1320
gtggaaaacc tcagccctga agaaggccca gcaggcctta agggtaagaa ggctgtgtac  1380
ctgggcgatg cgacaacaa catggccaac tcctacatga ttggctttgc caccgcgggc  1440
atggatattt ccatcatcgc tcctgaaggg ttccagcctc gtgcggaatt cgtggagcgc  1500
gcggaaaagc gtggccagga aaccggcgcg aaggttgttg tcaccgacag cctcgacgag  1560
gttgccggcg ccgatgttgt catcaccgat acctgggtat ccatgggtat ggaaaacgac  1620
ggcatcgatc gcaccacacc tttcgttcct taccaggtca acgatgaggt catggcgaaa  1680
gctaacgacg gcgccatctt cctgcactgc cttcctgcct accgcggcaa agaagtggca  1740
gcctccgtga ttgatggacc agcgtccaaa gttttcgatg aagcagaaaa ccgcctccac  1800
gctcagaaag cactgctggt gtggctgctg gccaaccagc gaggtaaga c atg tct   1857
                                                      Met Ser
                                                        1 ctt ggc tca acc ccg tca aca ccg gaa aac tta aat ccc gtg act cgc   1905
Leu Gly Ser Thr Pro Ser Thr Pro Glu Asn Leu Asn Pro Val Thr Arg
       5                  10                  15 act gca cgc caa gct ctc att ttg cag att ttg gac aaa caa aaa gtc   1953
Thr Ala Arg Gln Ala Leu Ile Leu Gln Ile Leu Asp Lys Gln Lys Val
   20                  25                  30 acc agc cag gta caa ctg tct gaa ttg ctg ctg gat gaa ggc atc gat   2001
Thr Ser Gln Val Gln Leu Ser Glu Leu Leu Leu Asp Glu Gly Ile Asp
35                  40                  45                  50 atc acc cag gcc acc ttg tcc cgg gat ctc gat gaa ctc ggt gca cgc   2049
Ile Thr Gln Ala Thr Leu Ser Arg Asp Leu Asp Glu Leu Gly Ala Arg
               55                  60                  65
```

```
aag gtt cgc ccc gat ggg gga cgc gcc tac tac gcg gtc ggc cca gta      2097
Lys Val Arg Pro Asp Gly Gly Arg Ala Tyr Tyr Ala Val Gly Pro Val
            70                  75                  80 gat agc atc gcc cgc gaa gat ctc cgg ggt ccg tcg gag aag ctg cgc      2145
Asp Ser Ile Ala Arg Glu Asp Leu Arg Gly Pro Ser Glu Lys Leu Arg
                85                  90                  95 cgc atg ctt gat gaa ctg ctg gtt tct aca gat cat tcc ggc aac atc      2193
Arg Met Leu Asp Glu Leu Leu Val Ser Thr Asp His Ser Gly Asn Ile
            100                 105                 110 gcg atg ctg cgc acc ccg ccg gga gct gcc cag tac ctg gca agt ttc      2241
Ala Met Leu Arg Thr Pro Pro Gly Ala Ala Gln Tyr Leu Ala Ser Phe
115                 120                 125                 130 atc gat agg gtg ggg ctg aaa gaa gtc gtt ggc acc atc gct ggc gat      2289
Ile Asp Arg Val Gly Leu Lys Glu Val Val Gly Thr Ile Ala Gly Asp
                135                 140                 145 gac acc gtt ttt gtt ctc gcc cgt gat ccg ctc aca ggt aaa gaa cta      2337
Asp Thr Val Phe Val Leu Ala Arg Asp Pro Leu Thr Gly Lys Glu Leu
            150                 155                 160 ggt gaa tta ctc agc ggg cgc acc act taaagcgccc ctagttcaag            2384
Gly Glu Leu Leu Ser Gly Arg Thr Thr
            165                 170 gcttgttaat cgcttgttaa tgcaggcagg taaggtataa cccgagtgtt ttttcgagga    2444
ataccaaccc tttcaacaca ataatttct ttaaacatcc ttgctgtcca ccacggctgg     2504
caaggaactt aaaatgaagg agcacacctc atgactaacc gcatcgttct tgcatactcc    2564
ggcggtctgg acaccactgt ggcaattcca tacctgaaga agatgattga tggtgaagtc    2624
atcgcagttt ctctcgacct gggccagggt ggagagaaca tggacaacgt tcgccagcgt    2684
gcattggatg ccggtgcagc tgagtccatc gttgttgatg caaaggatga gttcgctgag    2744
gagtactgcc tgccaaccat caaggcaaac ggcatgtaca tgaagcagta cccactggtt    2804
tctgcaatct cccgcccact gatcgtcaag cacctcgttg aggctggcaa gcagttcaac    2864
ggtacccacg ttgcacacgg ctgcactggt aagggcaacg accaggttcg tttcgaggtc    2924
ggcttcatgg acaccgatcc aaacctggag atcattgcac ctgctcgtga cttcgcatgg    2984
acccgcgaca aggctatcgc cttcgccgag gagaacaacg ttccaatcga gcagtccgtg    3044
aagtccccat tctccatcga ccagaacgtc tggggccgcg ctattgagac cggttacctg    3104
gaagatctgt ggaatgctcc aaccaaggac atctacgcat acaccgagga tccagctctg    3164
ggtaacgctc cagatgaggt catcatctcc ttcgagggtg gcaagccagt ctccatcgat    3224
ggccgtccag tctccgtact gcaggctatt gaagagctga accgtcgtgc aggcgcacag    3284
ggcgttggcc gccttgacat ggttgaggac cgtctcgtgg gcatcaagtc ccgcgaaatc    3344
tacgaagcac caggcgcaat cgcactgatt aaggctcacg aggctttgga agatgtcacc    3404
atcgagcgcg aactggctcg ctacaagcgt ggcgttgacg cacgtgggc tgaggaagta    3464
tacgacggcc tgtggttcgg acctctgaag cgctccctgg acgcgttcat tgattccacc    3524
caggagcacg tcaccggcga tatccgcatg gttctgcacg caggttccat caccatcaat    3584
ggtcgtcgtt ccagccactc cctgtacgac ttcaacctgg ctacctacga caccggcgac    3644
accttcgacc agaccctggc taagggcttt gtccagctgc acggtctgtc ctccaagatc    3704
gctaacaagc gcgatcgcga agctggcaac aactaagcca ccttttcaag catccagact    3764
agaacttcaa gtatttagaa agtagaagaa caccacatgg aacagcacgg aaccaatgaa    3824
ggtgcgctgt ggggcggccg cttctccggt ggaccctccg aggccatgtt cgccttgagt    3884
```

```
gtctccactc atttcgactg ggttttggcc ccttatgatg tgttggcctc caaggcacac    3944
gccaaggttt tgcaccaagc agagctactt tctgatgaag atctagccac catgctggct    4004
ggtcttgatc agctgggcaa ggatgtcgcc gacggaacct tcggtccgct gccttctgat    4064
gaggatgtgc acggcgcgat ggaacgcggt ctgattgacc gcgttggtcc tgaggtgggc    4124
ggccgtctgc gcgctggtcg ttcccgcaac gaccaggtgg caaccctgtt ccgcatgtgg    4184
gtccgcgacg cagtgcgcga catcgcgctg gaacaaccg agcttgtcga c              4235
```

<210> SEQ ID NO 18
<211> LENGTH: 171
<212> TYPE: PRT
<213> ORGANISM: Brevibacterium flavum

<400> SEQUENCE: 18

```
Met Ser Leu Gly Ser Thr Pro Ser Thr Pro Glu Asn Leu Asn Pro Val
1               5                   10                  15

Thr Arg Thr Ala Arg Gln Ala Leu Ile Leu Gln Ile Leu Asp Lys Gln
            20                  25                  30

Lys Val Thr Ser Gln Val Gln Leu Ser Glu Leu Leu Leu Asp Glu Gly
        35                  40                  45

Ile Asp Ile Thr Gln Ala Thr Leu Ser Arg Asp Leu Asp Glu Leu Gly
    50                  55                  60

Ala Arg Lys Val Arg Pro Asp Gly Gly Arg Ala Tyr Tyr Ala Val Gly
65                  70                  75                  80

Pro Val Asp Ser Ile Ala Arg Glu Asp Leu Arg Gly Pro Ser Glu Lys
                85                  90                  95

Leu Arg Arg Met Leu Asp Glu Leu Leu Val Ser Thr Asp His Ser Gly
            100                 105                 110

Asn Ile Ala Met Leu Arg Thr Pro Pro Gly Ala Ala Gln Tyr Leu Ala
        115                 120                 125

Ser Phe Ile Asp Arg Val Gly Leu Lys Glu Val Val Gly Thr Ile Ala
    130                 135                 140

Gly Asp Asp Thr Val Phe Val Leu Ala Arg Asp Pro Leu Thr Gly Lys
145                 150                 155                 160

Glu Leu Gly Glu Leu Leu Ser Gly Arg Thr Thr
                165                 170
```

<210> SEQ ID NO 19
<211> LENGTH: 25
<212> TYPE: DNA
<213> ORGANISM: Artificial Sequence
<220> FEATURE:
<223> OTHER INFORMATION: synthetic DNA

<400> SEQUENCE: 19

```
cccgggtttt cttctgcaac tcggg                                           25
```

<210> SEQ ID NO 20
<211> LENGTH: 25
<212> TYPE: DNA
<213> ORGANISM: Artificial Sequence
<220> FEATURE:
<223> OTHER INFORMATION: synthetic DNA

<400> SEQUENCE: 20

```
gtcgacaagc tcggttgttc ccagc                                           25
```

<210> SEQ ID NO 21

```
<211> LENGTH: 24
<212> TYPE: DNA
<213> ORGANISM: Artificial Sequence
<220> FEATURE:
<223> OTHER INFORMATION: synthetic DNA

<400> SEQUENCE: 21
cccctagttc aaggcttgtt aatc                                              24

<210> SEQ ID NO 22
<211> LENGTH: 25
<212> TYPE: DNA
<213> ORGANISM: Artificial Sequence
<220> FEATURE:
<223> OTHER INFORMATION: synthetic DNA

<400> SEQUENCE: 22
gtcttacctc ggctggttgg ccagc                                             25
```